(12) United States Patent
Igarashi

(10) Patent No.: US 7,678,045 B2
(45) Date of Patent: Mar. 16, 2010

(54) ENDOSCOPE OPTICAL SYSTEM

(75) Inventor: Tsutomu Igarashi, Hachioji (JP)

(73) Assignee: Olympus Corporation, Tokyo (JP)

( * ) Notice: Subject to any disclaimer, the term of this patent is extended or adjusted under 35 U.S.C. 154(b) by 1100 days.

(21) Appl. No.: 11/271,749

(22) Filed: Nov. 14, 2005

(65) Prior Publication Data

US 2007/0149854 A1    Jun. 28, 2007

(30) Foreign Application Priority Data

Nov. 19, 2004  (JP) ............... 2004-336195

(51) Int. Cl.
*A61B 1/00* (2006.01)
*A61B 1/04* (2006.01)
*A61B 1/06* (2006.01)

(52) U.S. Cl. ............... 600/160; 600/129; 600/167

(58) Field of Classification Search ........... 600/101, 600/129, 160, 176, 178; 348/65, 71
See application file for complete search history.

(56) References Cited

U.S. PATENT DOCUMENTS

| | | | | |
|---|---|---|---|---|
| 4,959,710 A | * | 9/1990 | Uehara et al. ............... 600/109 |
| 4,983,019 A | * | 1/1991 | Ikuno et al. ................. 600/181 |
| 5,001,556 A | * | 3/1991 | Nakamura et al. ........... 348/70 |
| 5,512,940 A | * | 4/1996 | Takasugi et al. ............. 348/71 |
| 2003/0139650 A1 | * | 7/2003 | Homma ..................... 600/181 |
| 2003/0176768 A1 | * | 9/2003 | Gono et al. ................. 600/109 |
| 2003/0229270 A1 | * | 12/2003 | Suzuki et al. .............. 600/178 |
| 2007/0027362 A1 | * | 2/2007 | Handa et al. ............... 600/160 |
| 2007/0230312 A1 | * | 10/2007 | Ikenaka ................. 369/112.26 |

FOREIGN PATENT DOCUMENTS

| | | |
|---|---|---|
| JP | 3-24848 | 4/1991 |
| JP | 2000-262459 | 9/2000 |
| JP | 2001-170009 | 6/2001 |
| JP | 2003-215469 | 7/2003 |

* cited by examiner

*Primary Examiner*—John P Leubecker
*Assistant Examiner*—Philip R Smith
(74) *Attorney, Agent, or Firm*—Kenyon & Kenyon LLP

(57) ABSTRACT

An endoscope observation optical system capable of improving the observation resolution of a mucous membrane of a living body is provided. The endoscope includes an observation optical system compatible with both standard visible-light observation and blood-vessel-enhancement observation, whose main component of a displayed image is an absorption peak of hemoglobin present in a waveband lower than 480 nm, wherein some longitudinal chromatic aberration remains in the endoscope observation optical system due to undercorrection at a wavelength of 415 nm, and wherein the focal position during blood-vessel-enhancement observation is set closer to a near point than the focal position during standard visible-light observation.

2 Claims, 5 Drawing Sheets

B2 IMAGE　　　　G2 IMAGE　　　　R2 IMAGE

ENDOSCOPE OPTICAL SYSTEM

BACKGROUND OF THE INVENTION

1. Field of the Invention

The present invention relates to a frame-sequential or a synchronous endoscope and, more specifically, relates to an observation optical system of an endoscope having a blood-vessel-enhancement observation function or a mucous-membrane slice-image observation function.

The present application is based on Japanese Patent Application No. 2004-336195, the content of which is incorporated by reference.

2. Description of Related Art

For frame-sequential or synchronous endoscopes having a blood-vessel-enhancement observation function or a mucous-membrane slice-image observation function, endoscopes capable of carrying out, for example, standard visible-light observation, predetermined-waveband-enhancement observation, blood-vessel-enhancement observation, or mucous-membrane deep-slice image observation are known.

Here, standard visible-light observation uses standard observation conditions for image acquisition using light in the entire visible range. Predetermined-waveband-enhancement observation uses conditions in which a predetermined wavelength band is enhanced by an optical filter or a predetermined waveband is displayed with enhancement by carrying out inter-band calculations on a plurality of acquired color band images. Blood-vessel-enhancement observation is a type of predetermined-waveband-enhancement observation in which a waveband that is optimal for the absorption characteristics of blood is emphasized. Mucous-membrane deep-slice image observation uses conditions in which one mucous-membrane slice image is selected from a plurality of mucous-membrane slice images having different depths and observed.

In the related art, an endoscope showing improved ability to observe a mucous membrane of a living organism by predetermined-waveband-enhancement observation include the technologies disclosed in Japanese Examined Patent Application Publication No. HEI-3-24848 and Japanese Unexamined Patent Application Publication Nos. 2000-262459 and 2001-170009. According to the related art, blood-vessel-enhancement observation, in which the spectrum of illuminating rays is optimized for hemoglobin, is capable of enhanced display of blood vessel flow. However, in the related art, the illumination and the image calculation method after image acquisition are the main issues, and observation optical systems configured to form an image of an object on an image-acquisition device have not been taken into sufficient consideration.

Japanese Unexamined Patent Application Publication No. 2003-215469 describes features related to the spectral transmittance in the vicinity of the pupil of a videoscope objective optical system. However, the aberrations of the objective optical system and the wavelength dependency of the focus setting have not been taken into sufficient consideration.

In a known observation optical system in which only standard visible-light observation has been considered, the observing ability could be improved by providing a design with the smallest aberration possible. However, there was a problem in that, for an endoscope carrying out predetermined-waveband-enhancement observation, such as that discussed in the above-cited related art documents, reducing the aberration may not be the best approach.

In particular, in relation to magnified observation, whose need has been increasing recently, two cases in which the application of a known observation optical system in pursuing reduction in aberration is not desirable will be described below.

(1) In blood-vessel-enhancement observation, since a lesion is diagnosed based mainly on the condition of the capillary blood vessel flow at the surface of a mucous membrane, a high observation magnification is required for resolving a minute pattern. Therefore, in blood-vessel-enhancement observation, it is desirable to use a magnification higher than that used in standard visible-light observation. However, for an observation optical system whose aberrations have been completely corrected, the optical specifications for the blood-vessel-enhancement observation and the standard visible-light observation become the same. Thus, there is a problem in that the magnification cannot be increased.

(2) Research on carrying out in-vivo image analysis of a mucous membrane has been carried out. In such an application, an ultra-high-magnification optical system having a significantly narrow depth of field is used, wherein, to prevent blurriness of the image, methods such as bringing the tip of the endoscope into contact with the mucous membrane of the living organism and fixing the position by attaching a tip attachment are used. When the aberrations are completely corrected in such an ultra-high-magnification observation optical system, the focal position of the object does not depend on wavelength. For this reason, it is impossible to carry out the above-mentioned mucous-membrane deep-slice image observation function since image information only on the surface or a single predetermined slice image at a certain depth can be obtained. Under these conditions, image analysis of each mucous layer and/or invasion diagnosis of the lesion cannot be carried out. Furthermore, if a focusing mechanism is provided, theoretically, the depth can be changed. However, it is difficult to provide a focusing mechanism in a small-diameter endoscope. Moreover, the focusing operation is difficult for the user to carry out, and, thus, it has little practicality.

BRIEF SUMMARY OF THE INVENTION

In order to solve the above-described problems, an object of the present invention is to provide an endoscope observation optical system capable of improving the observation resolution of a mucous membrane of a living body.

More specifically, a first object is to provide a structure that is capable of increasing the magnification of blood-vessel-enhancement observation compared to that of standard visible-light observation, and a second object is to provide a structure that is capable of realizing mucous-membrane deep-layer slice-image observation without a focusing mechanism.

In order to attain the forgoing object, the present invention provides the following solutions.

According to a first aspect, the present invention provides an endoscope including an observation optical system compatible with both standard visible-light observation and blood-vessel-enhancement observation whose main component of a displayed image is an absorption peak of hemoglobin present in a waveband lower than 480 nm, wherein the focal position of the endoscope observation optical system during blood-vessel-enhancement observation is set closer to a near point than the focal position during standard visible-light observation by allowing some longitudinal chromatic aberration to remain in the observation optical system due to undercorrection at a wavelength of 415 nm.

Since the focal position during blood-vessel-observation is set closer to a near point than the focal position during standard visible-light observation by allowing some longitudinal chromatic aberration to remain in the observation optical system according to a first aspect of the present invention due to undercorrection at a wavelength of 415 nm, the magnification range in which focusing is possible in blood-vessel-enhancement observation using light typified by 415 nm light can be shifted to the magnifying side compared to standard visible-light observation.

According to a second aspect, the present invention provides an endoscope including an observation optical system compatible with both standard visible-light observation and blood-vessel-enhancement observation, whose main component of a displayed image is an absorption peak of hemoglobin present in a waveband lower than 480 nm, wherein the endoscope observation optical system satisfies Formula (1) below for the focal position during standard visible-light observation:

$$-0.25<\Delta[415]/f<-0.02 \qquad (1)$$

where $\Delta[415]$ represents the longitudinal chromatic aberration of light having a wavelength of 415 nm (when light having a wavelength of 546 nm is used as a reference), and f represents the focal length of the entire observation optical system for light having a wavelength of 546 nm.

According to the second aspect of the present invention, since the characteristics of the observation optical system are set to satisfy $\Delta[415]/f<-0.02$, sufficient magnified observation can be carried out during blood-vessel-enhancement observation, and, since $-0.25<\Delta[415]/f$, the longitudinal chromatic aberration can be prevented from becoming too great, and the contrast in standard visible-light observation can be prevented from being reduced.

According to the second aspect of the present invention, it is preferable that the observation optical system satisfy Formula (2) below:

$$-0.15<\Delta[415]/f<-0.05 \qquad (2)$$

In this way, since the characteristics of the observation optical system are set to satisfy $\Delta[415]/f<-0.05$, the magnification is improved, and, since $-0.15<\Delta[415]/f$, for example, when the observation optical system is used as an observation optical system for a high quality endoscope using a high-resolution image-acquisition device, the image quality for standard visible-light observation is prevented from deteriorating due to the longitudinal chromatic aberration becoming too great.

According to a third aspect, the present invention provides an endoscope including an observation optical system capable of magnified observation in which the absolute value of the paraxial magnification is 0.5 or more, wherein the longitudinal chromatic aberration is set so that the observation optical system will satisfy Formula (3) below in a magnified observation state:

$$0.05 \text{ mm}<WD[546]-WD[415]<0.75 \text{ mm} \qquad (3)$$

where WD[546] represents the focused object distance of light having a wavelength of 546 mm, and WD[415] represents the focused object distance of light having a wavelength of 415 mm.

According to the third aspect of the present invention, since the characteristics of the observation optical system are set to satisfy as 0.05 mm<WD[546]−WD[415], the mucous layer can be identified while maintaining the movement of the focal position for each wavelength, and, since WD[546]−WD[415] <0.75 mm, the resolution in the depth direction is prevented from being too coarse.

Since the focal position during blood-vessel-enhancement observation is set closer to a near point than the focal position during standard visible-light observation by allowing some longitudinal chromatic aberration to remain in the endoscope observation optical system according to the present invention due to undercorrection at a wavelength of 415 nm, an advantage is provided in that the magnification of the blood-vessel-enhancement observation can be increased compared to that of standard visible-light observation.

Moreover, with the endoscope observation optical system according to the present invention, since the longitudinal chromatic aberration of the observation optical system is set so that Formula (3) is satisfied in a magnified observation state, mucous-membrane deep-layer slice-image observation can be realized without a focusing mechanism.

DETAILED DESCRIPTION OF THE INVENTION

First, blood-vessel-enhancement observation assumed in the present invention will be described in general, and, then, each embodiment of the present invention will be described.

First, the waveband to be used in blood-vessel-enhancement observation will be described on the basis of the characteristics of a mucous membrane of a living body, which is the object to be imaged.

Figure 1:
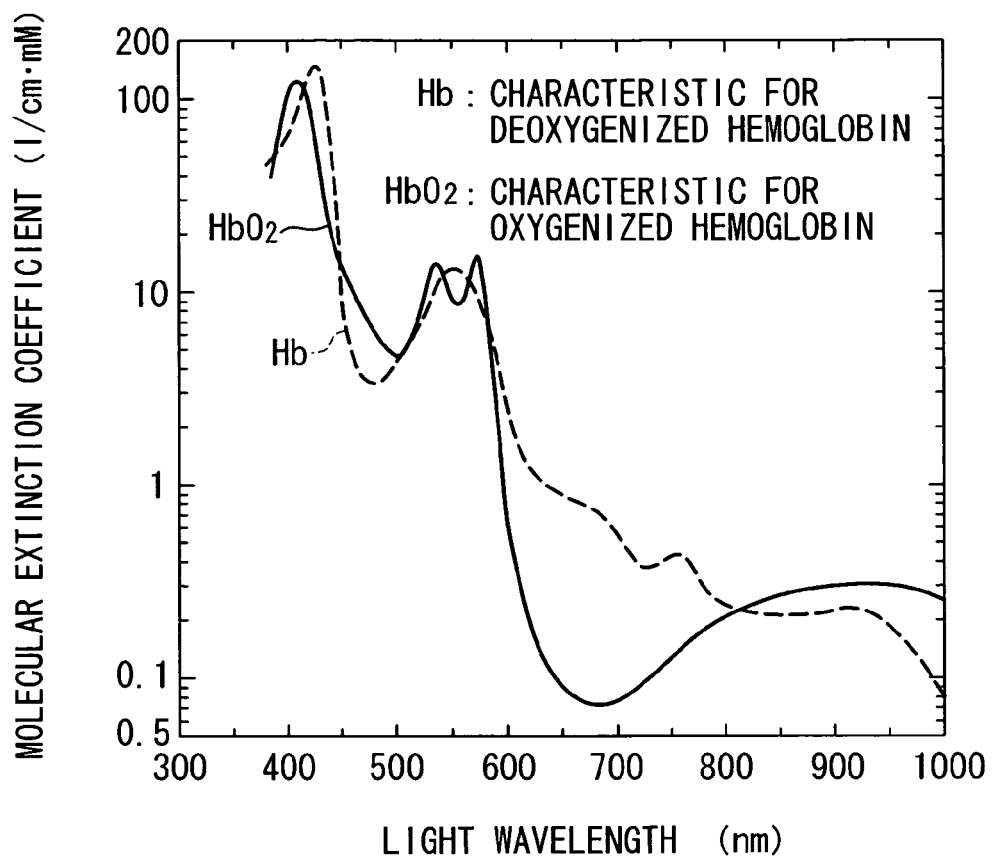
FIG. 1 illustrates the absorption characteristics of hemoglobin.

FIG. 1 illustrates the absorption characteristics of hemoglobin. Hemoglobin exists in two different states depending on the presence of oxygen. In either state, in general, in the visible range, absorption of shorter wavelengths is strong, and absorption of longer wavelengths is weak. More specifically, the absorption peak exists below 480 nm.

Figure 2A:
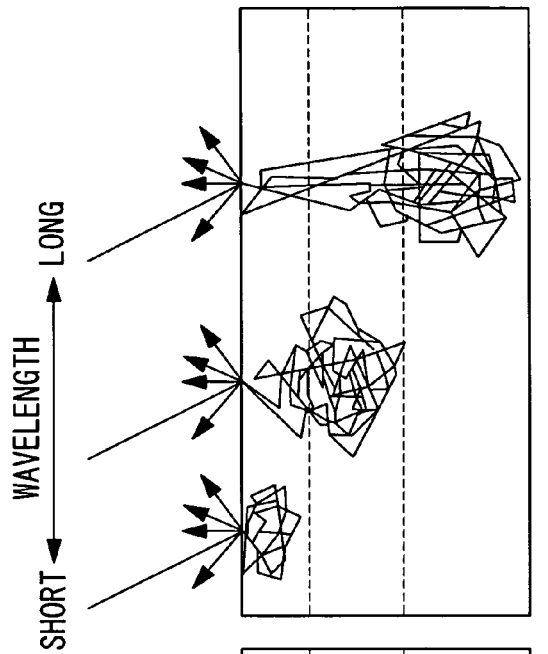
FIG. 2A is a cross-sectional schematic view of a mucous membrane of a living organism having many blood vessels.
Figure 2B:
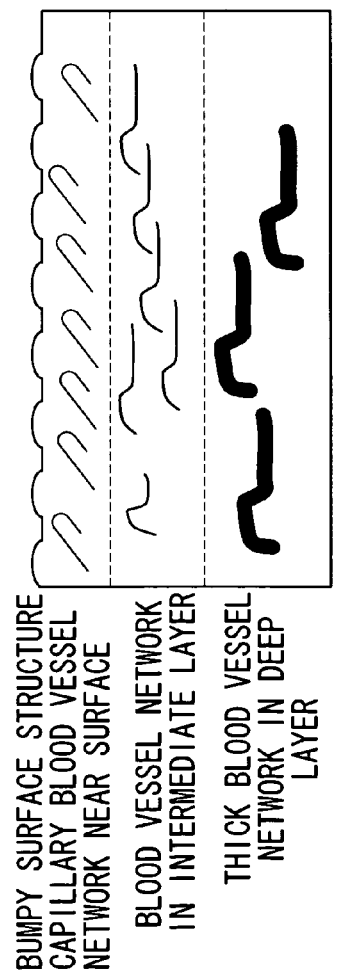
FIG. 2B illustrates the invasion depth of light in the mucous membrane of a living organism.

FIG. 2 illustrates a schematic view of the mucous layers of a living organism and the invasion depth of light. FIG. 2A is a cross-sectional schematic view of a mucous membrane of a living body including many blood vessels and illustrates, in order from the surface, a bumpy structure and capillary vessels, blood vessels larger than the capillary vessels present in a deeper layer, and even larger blood vessels present in an even deeper layer. FIG. 2B illustrates the invasion depth of light in the mucous membrane of a living organism. In the visible range, as the wavelength of light becomes shorter, the invasion depth becomes shallower, and as the wavelength of light becomes longer, the invasion depth becomes deeper.

This is because the absorption characteristic of hemoglobin (refer to FIG. 1) is high at shorter wavelengths and because dispersion due to the cell structure is greater at shorter wavelengths.

Therefore, by using short-wavelength light, the bumpy structure near the surface of the mucous membrane and images of capillary vessels can be observed. Since short-wavelength light is included in a waveband having high hemoglobin absorption, the background appears as a bright image and the blood vessels appear as a dark image, and high contrast observation is thus possible. However, since the invasion depth is shallow, most blood vessels in deep layers are not included in the image.

When long-wavelength light is used, since the invasion depth is deep, images of large blood vessel in deep layers can be observed. However, since long-wavelength light is included in a waveband having low hemoglobin absorption, the contrast of the blood vessel image is lower than that obtained at shorter wavelengths.

Therefore, to simply carry out enhancement observation of capillary blood vessels near the surface, it is most effective to capture an image with the shorter waveband enhanced. Moreover, this is advantageous since, the shorter the wavelength, the more the modulation transfer function (MTF) of the observation optical system can be improved, based on the principles of wave optics, and high resolution and high contrast are thus achieved.

Next, improvement of visibility on the monitor of the blood vessel image captured in the short waveband will be described.

The relative luminosity and resolution in visible observation is highest for green (G band), next highest for red (R band), and lowest for blue (B band). Abundant blood vessel information is included in the B band. In standard visible-light observation, the captured B-band image including the abundant blood vessel information is displayed on the monitor as a B band. Since blood vessel information in the B band, for which the human visual sensitivity is low, is displayed in standard visible-light observation, improvement in visibility of the blood vessel information cannot be realized.

Accordingly, a method of improving the blood vessel visibility without using the spectral characteristics will be described below.

Here, frame-sequential blood-vessel-enhancement observation will be described.

Figure 3A:
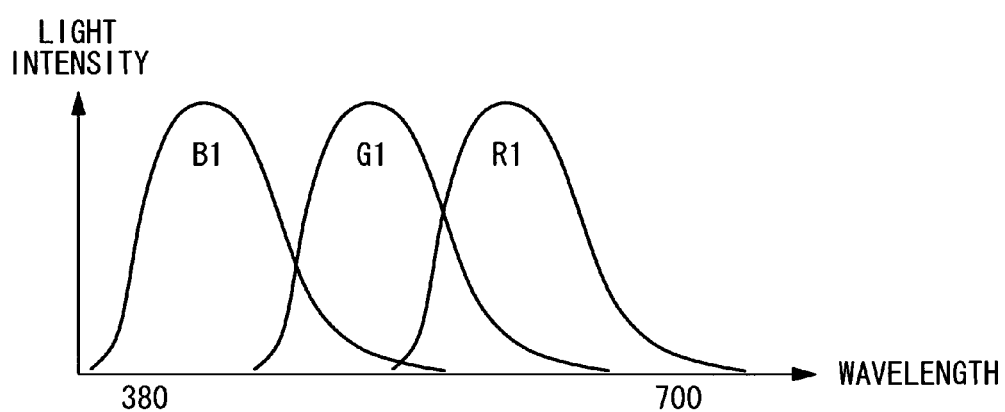
FIG. 3A illustrates typical illumination spectral intensity characteristics for standard visible-light observation.

FIG. 3 illustrates the illumination spectral intensity characteristics in an RGB time-division system of a frame-sequential light source apparatus. FIG. 3A illustrates typical illumination spectral intensity characteristics for standard visible-light observation, wherein image-acquisition bands, R1, G1, and B1, are set as relatively wide bands so that gaps are not generated at the band borders.

For standard visible-light observation, connections are established so that the monitor display bands and the image-acquisition bands have the following relationships so as to obtain accurate color reproducibility. More specifically, an image signal processed through a circuit on the video processor side is output and connected to the monitor.

| Monitor Display Band | R (red) | G (green) | B (blue) |
| Captured Band | R1 | G1 | B1 |

The visibility of the blood vessels in this standard visible-light observation is not very good. This is because the image information in the B1 band including the most blood vessel information is displayed as a B band. Accordingly, the visibility of the blood vessel information will be improved if inter-band calculations are carried out so that the image information of the captured B1 band is included in the monitor G band, which is a band easily perceived by the human eye.

As a simplest example, blood-vessel-enhancement observation is possible by simple band shift and copy calculations (or line distribution and switching of the RGB output signals).

| | Monitor Display Band | | |
| | R (red) | G (green) | B (blue) |
| Captured Band | G1 | B1 | B1 |

In this example, the captured B1-band image whose blood vessel image has the highest contrast is displayed in two areas, i.e., the G band and the B band, on the monitor. Therefore, compared to the method in which the captured B1-band image is displayed only on the B band of the monitor, the contrast of the blood vessel image displayed on the monitor is significantly improved.

By allowing a captured G1-band image, having the second highest blood vessel image contrast, to be displayed in a monitor R band instead of a captured R1-band image, having the lowest blood-vessel image contrast, a captured image, having a high blood-vessel image contrast can be displayed in all display bands on the monitor, and thus the blood vessel image can be emphasized. In this way, the blood vessels are enhanced. In such a case, the color reproducibility is lost but pseudo color display is possible by combining the colors cyan (G+B) and red (R).

As described above, the visibility of the blood vessel structure can be improved without manipulating the spectral characteristics. However, the visibility of blood vessels can be further improved by manipulating the spectral characteristics in addition to the above-described the band calculation.

Figure 3B:
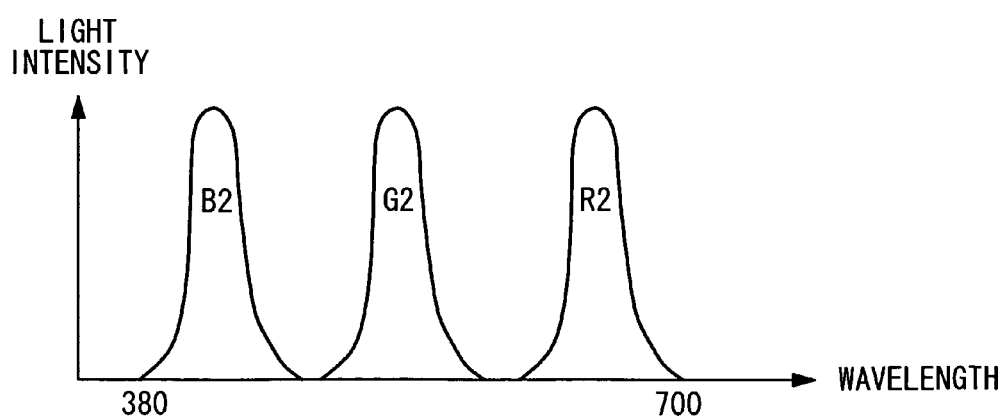
FIG. 3B illustrates an example of illumination spectral intensity characteristics for a blood vessel image having improved contrast by limiting wavebands to those having high absorption and cut-off wavebands having low absorption, which are low-contrast components.

FIG. 3B is one example in which the bands R2, G2, and B2 are set as narrow bands. According to the spectral characteristics illustrated in FIG. 3A, wavelengths having low absorption remain in the same captured band as a low-contrast component. Therefore, as in FIG. 3B, the contrast of the blood vessel image can be improved by cutting off the wavebands having low absorption, which are low contrast components, and limiting the waveband to wavebands having high absorption.

The central wavelength of the B2 band is set to about 415 nm so as to match the maximum absorption peak of hemoglobin. The central wavelength of the G2 band is set to about 550 nm, which is close to the second-strongest absorption peak of hemoglobin, or set between about 500 nm and about 540 nm, which is slightly toward shorter wavelengths, considering the difference with the R2 band.

The G2 band, set accordingly, can visualize a specific blood vessel located slightly deeper than the surface mucous layer. By carrying out setting of the B2 band and the G2 band and the above-described inter-band calculation, an ideal blood vessel contrast enhancement is possible for a relatively thin layer near the surface of the surface mucous layer.

Figure 4:
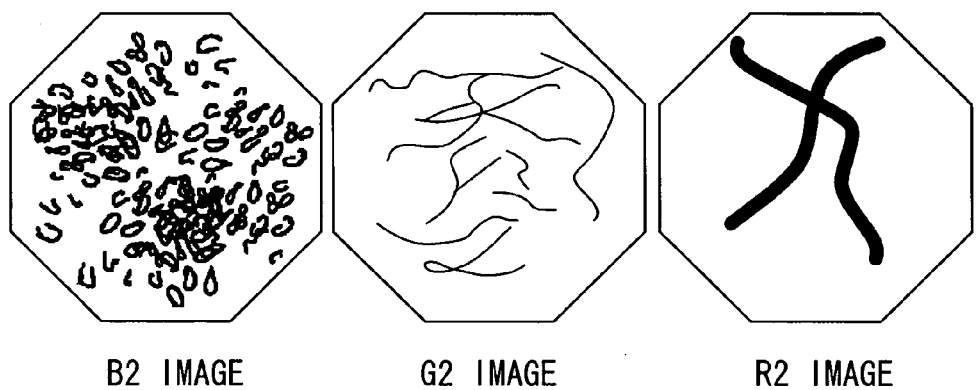
FIG. 4 illustrates an image in blood vessel enhancement.

The R2 band is in an area where the absorption of hemoglobin is low and does not contribute much to the blood vessel contrast enhancement near the surface layer. However, the R2 band becomes important when expanding the display color space or when obtaining an image of a blood vessel in a deep layer. In such a case, the R2 band is set to about 600 nm and is used for inter-band calculation. By carrying out image acquisition in this way, the structure of the mucous layers shown in FIG. 2 can be captured as an image of a mucous membrane with high contrast and high discrimination, as shown in FIG. 4.

In general, the image of the mucous membrane is reddish or yellowish due to the absorption characteristics of hemoglobin. Therefore, according to the spectral characteristics of the narrow band, in some cases, attention must be paid to the dynamic ranges of the captured band when setting the filter. In FIG. 3B, the spectral intensity integration values of the B2 band, the G2 band, and the R2 band are substantially the same value. By taking into consideration the intensity characteristics of the image of the mucous membrane and lowering the spectral intensity integration values of the G2 band and R2 band relative to that of the B2 band, oversaturation of the G2 band and the R2 band, which more easily become saturated than the B2 band, can be prevented.

In the above, blood-vessel-enhancement observation according to a frame-sequential system was described. The same principle can be applied to a synchronous system using a color image-acquisition device. For a synchronous system, an on-chip color filter disposed inside the image-acquisition device replaces the characteristics of the B1 band, the G1 band, and the R1 band, shown in FIG. 3A. Therefore, the illumination light may be regular white light, such as xenon lamp light. When narrowing the band for blood vessel enhancement in a synchronous system, the B2, G2, and R2 bands may be provided simultaneously, instead of in a time-division manner, as illumination light, and a white light source and an optical filter having transmissive bands for the B2, G2, and R2 bands, shown in FIG. 3B, may be combined.

The color image-acquisition device is not only provided for a primary color system but is also provided for a complementary color system. Even when a complementary color system is used, the complementary colors are converted into RGB in the video processor. Therefore, even when the above-described principle is applied to the complementary color system, it is not a serious problem, and the inter-band calculation may be carried out after the RGB conversion to enhance the images of the B1 band and the B2 band for display.

As described above, blood-vessel-enhancement observation is possible by carrying out inter-band calculation for enhanced display of a captured B band image and, moreover, by narrowing the bands in the spectral characteristics for the standard visible-light observation.

First Embodiment

A first embodiment of the present invention will be described below with reference to FIGS. 5 and 6 and data according to examples.

The observation optical system according to the present invention refers to the entire optical system forming an image of an object on the image-acquisition device. Thus, for a so-called videoscope having an image-acquisition device provided at the insertion end, the objective optical system is the observation optical system. Moreover, for a combination of a rigid endoscope having an objective optical system and a relay optical system in the insertion part and a television camera having an image-acquisition device, the entire optical system from the end of the rigid endoscope to the image-acquisition device in the television camera is viewed as the observation optical system.

In this embodiment, to simplify the description, an example objective optical system of a videoscope will be described.

First, a known observation optical system will be described, and, subsequently, the observation optical system according to this embodiment will be described in comparison with the known observation optical system.

Figure 5:
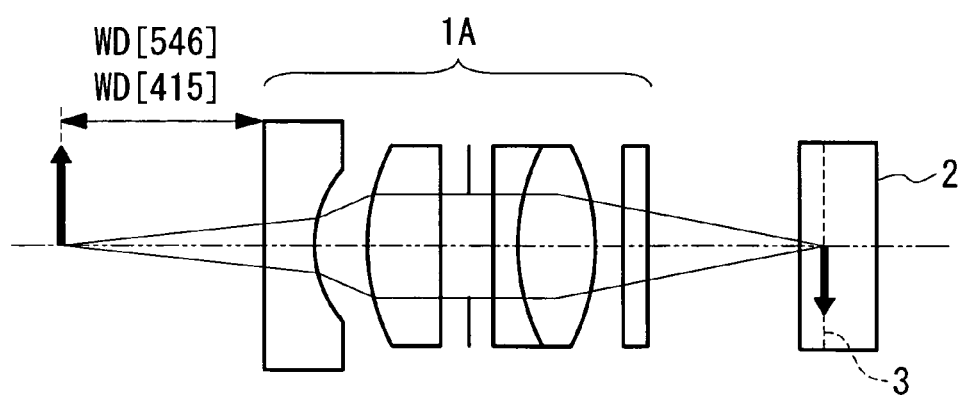
FIG. 5 is a schematic view of a known observation optical system with corrected longitudinal chromatic aberration.

FIG. 5 illustrates the scheme of a known observation optical system whose longitudinal chromatic aberration has been sufficiently corrected. According to the example shown in FIG. 5, a fixed-focus objective optical system for a videoscope is the observation optical system. The basic structure of the observation optical system shown in FIG. 5 is the same as that of the observation optical system according to the first embodiment of the present invention. The observation optical system according to the first embodiment differs only in the correction of the longitudinal chromatic aberration.

An objective optical system 1A including a plurality of lenses and an aperture stop, as shown in FIG. 5, is configured to form an image of an object on an image-acquisition device 2. For standard visible-light observation, the focal position is located at an image-acquisition plane 3 of the image-acquisition device 2 for a light having a wavelength of 546 nm (e-line), which is the central wavelength of the visible range. In this case the focused object distance is represented as WD[546].

The central wavelength of the maximum absorption peak of hemoglobin is assumed to be 415 nm (refer to FIG. 1), and the relationship between the focused object distances WD[415] of light having a wavelength of 415 nm and WD[546] is WD[415]=WD[546] when there is no longitudinal chromatic aberration. This state is illustrated in FIG. 5. In this state, there is no difference in the magnification range in which focusing is possible in blood-vessel-enhancement observation using light represented by the 415 nm light and that of standard visible-light observation.

Next, the observation optical system according to this embodiment will be described.

Figure 6:
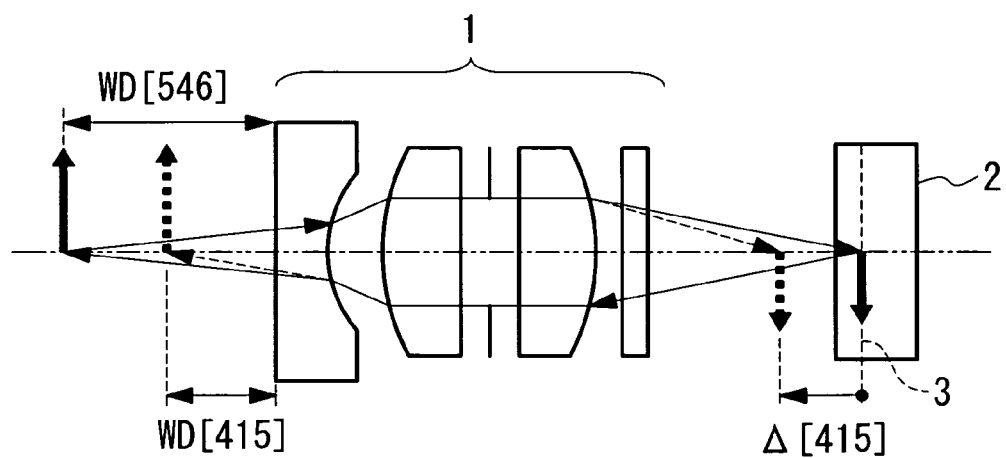
FIG. 6 illustrates the observation optical system according to the first embodiment of the present invention with residual longitudinal chromatic aberration.

FIG. 6 illustrates the observation optical system according to this embodiment with residual longitudinal chromatic aberration. More specifically, it illustrates the residual longitudinal chromatic aberration according to first to twelfth examples of this embodiment and illustrates the scheme of an observation optical system with longitudinal chromatic aberration remaining in a manner such that there is insufficient correction for blood-vessel-enhancement observation.

An objective optical system (observation optical system) 1 including a plurality of lenses and an aperture stop, as shown in FIG. 6, is configured to form an image of an object on an image-acquisition device 2. For standard visible-light observation, the focal position is positioned at an image-acquisition plane 3 of the image-acquisition device 2 for a light having a wavelength of 546 nm (e-line), which is the central wavelength of the visible range. For light having a wavelength of 415 nm, images are formed closer to the object than the image-acquisition plane 3.

In FIG. 6, the arrows of the heavy solid lines represent the object position and image position for light having a wavelength of 546 nm, and the arrows of the heavy dotted lines represent the object position and image position for light having a wavelength of 415 nm. In the drawings, the arrows of the thin lines represent the relationship between the start point and the end point during paraxial ray tracing. The arrow above the optical axis is traced from the focal position for the 546 nm light. The arrow below the optical axis is traced from the image plane 3 to the object side.

When the 415 nm light enters the objective optical system 1 from the focal position of the 546 nm light, the image of the 415 nm light is formed closer to the object than the image-acquisition plane because of the longitudinal chromatic aberration remaining in a manner such there is insufficient correction. In such a case, the longitudinal chromatic aberration is represented as $\Delta[415]$.

As a definition of the sign, the sign is negative when paraxial rays form an image on the object side with reference to the paraxial image plane (in this case, the image-acquisition plane 3) for a reference wavelength (in this case, 546 nm). In the case of FIG. 6, $\Delta[415]<0$. In this way, if image acquisition of an object present at the WD[546] position is carried out with 415 nm light, the image will be out of focus. However, by tracing the paraxial ray in the opposite direction from the image-acquisition plane, WD[415] can be calculated.

As is apparent from FIG. 6, when $\Delta[415]<0$, WD[415] <WD[546], and the focal position of the 415 nm light moves closer to the near-point. For this reason, compared to standard visible-light observation, the magnification range in which focusing is possible in blood-vessel-enhancement observation using light represented by the 415 nm light can be shifted towards magnifying side.

Table 1 shows design example data based on a known idea. Table 2 shows data according to the first to twelfth examples of the present invention.

focal point for blood-vessel-enhancement observation is shifted closer to the far point compared to standard visible-light observation.

According to the fourth and fifth known examples, $\Delta[415]/f<0$. However, since the absolute value is small, there is not a great difference between WD[546] and WD[415]. According to the first to fifth known examples, since WD[546]/WD[415] is less than one or about one, magnified observation cannot be carried out during blood-vessel-enhancement observation.

The first to twelfth examples shown in Table 2 all satisfy Formula (1), where $-0.25<\Delta[415]/f<-0.02$, and WD[546] >WD[415]. Even for the first example having the smallest absolute value of $\Delta[415]/f$, WD[546]/WD[415]=1.35, which is a potential improvement of the magnifying rate by 35%. Moreover, after the fifth example, the magnifying rate can be improved by a factor of two or more.

When $-0.02<\Delta[415]/f$, i.e., outside the range of Formula (1), similar to the above-described known examples, sufficient magnified observation cannot be carried out during blood-vessel-enhancement observation. In the case of $\Delta[415]/f<-0.25$, which is also outside the range of Formula (1), this is not preferable since the longitudinal chromatic aberration is too great and the contrast becomes too small in standard visible-light observation.

TABLE 1

| Example | Field angle | f | $\Delta[415]$ | $\Delta[415]/f$ | WD[546] | WD[415] | WD[546]/ WD[415] |
|---|---|---|---|---|---|---|---|
| 1 | 140° | 2.047 | 0.074 | 0.036 | 20 | 32.4 | 0.62 |
| 2 | 70° | 1.453 | 0.014 | 0.010 | 21 | 25.0 | 0.84 |
| 3 | 140° | 0.954 | 0.003 | 0.003 | 14.3 | 15 | 0.95 |
| 4 | 70° | 2.340 | −0.005 | −0.002 | 35 | 33.8 | 1.04 |
| 5 | 110° | 1.007 | −0.008 | −0.008 | 10.2 | 9.4 | 1.09 |

TABLE 2

| Example | Field angle | f | $\Delta[415]$ | $\Delta[415]/f$ | WD[546] | WD[415] | WD[546]/ WD[415] |
|---|---|---|---|---|---|---|---|
| 1 | 90° | 1.903 | −0.043 | −0.023 | 26.6 | 19.7 | 1.35 |
| 2 | 120° | 0.983 | −0.034 | −0.035 | 10 | 7.1 | 1.41 |
| 3 | 120° | 0.983 | −0.053 | −0.053 | 10 | 6.1 | 1.64 |
| 4 | 120° | 0.983 | −0.063 | −0.063 | 10 | 5.7 | 1.75 |
| 5 | 120° | 0.523 | −0.046 | −0.046 | 5.4 | 2.5 | 2.16 |
| 6 | 120° | 0.983 | −0.097 | −0.097 | 10 | 4.5 | 2.22 |
| 7 | 90° | 1.171 | −0.121 | −0.121 | 10.3 | 5.0 | 2.06 |
| 8 | 120° | 0.564 | −0.080 | −0.080 | 10 | 2.3 | 4.35 |
| 9 | 90° | 0.669 | −0.099 | −0.099 | 10 | 2.6 | 3.85 |
| 10 | 120° | 0.552 | −0.091 | −0.091 | 9.0 | 1.9 | 4.74 |
| 11 | 120° | 0.556 | −0.096 | −0.096 | 4.8 | 1.5 | 3.20 |
| 12 | 120° | 0.983 | −0.229 | −0.229 | 10 | 2.3 | 4.35 |

In Tables 1 and 2, $\Delta[415]/f$ represents $\Delta[415]$ normalized by a focal length f of the optical system. A comparison of this value to WD[546], WD[415], and WD[546]/WD[415] will be described.

Since the magnification of an optical system is inversely related to the observation distance, WD[546]/WD[415] can be viewed as a parameter representing the improvement in magnifying rate in blood-vessel-enhancement observation compared to standard visible-light observation. If WD[546]/ WD[415] is larger than one, the magnifying rate is improved.

According to the first to third known examples in Table 1, $\Delta[415]/f>0$ and WD[546]<WD[415]. In other words, the The most preferable range of $\Delta[415]/f$ is $-0.15<\Delta[415]/f<-0.05$, as indicated by Formula (2). The third to ninth examples correspond to this range.

When $-0.05<\Delta[415]/f$, i.e., outside the range of Formula (2), improvement in the magnifying rate is somewhat inadequate. When $\Delta[415]/f<-0.15$, i.e., also outside the range of Formula (2), the longitudinal chromatic aberration is too great for a high-image-quality endoscope using a high-resolution image-acquisition device, and the image quality becomes less acceptable in standard visible-light observation.

By using the objective optical system according to the first to twelfth examples, the magnifying rate for blood-vessel-enhancement observation is significantly improved relative to the standard visible-light observation, and the functions of a known objective optical system having a focus and zoom function can be realized even though the focus is fixed. Accordingly, the structure according to this embodiment is useful in that it enables small-diameter endoscopes on which movable lens parts cannot be easily mounted and highly resistant endoscopes compatible with autoclave sterilization to have a pseudo magnified observation function.

Second Embodiment

The structure according to a second embodiment of the present invention will be described with reference to thirteenth to eighteenth examples, on the assumption that mucous-membrane deep-layer slice-image observation is to be carried out.

The first to twelfth examples according to the above-described first embodiment are typical wide-angle observation optical system in endoscope since the wide-angle objective optical system (observation optical system) 1 has a wide depth of field, the information resolving ability in the optical axis direction is low. Thus, the objective optical system 1 is not suitable for mucous-membrane deep-layer slice-image observation.

On the other hand, by using an optical system having high magnification and narrow depth of field specifically for magnifying (microscope optical system), as shown in the thirteenth to eighteenth examples according to the second embodiment, mucous-membrane deep-layer slice-image observation can be carried out.

Figure 7:
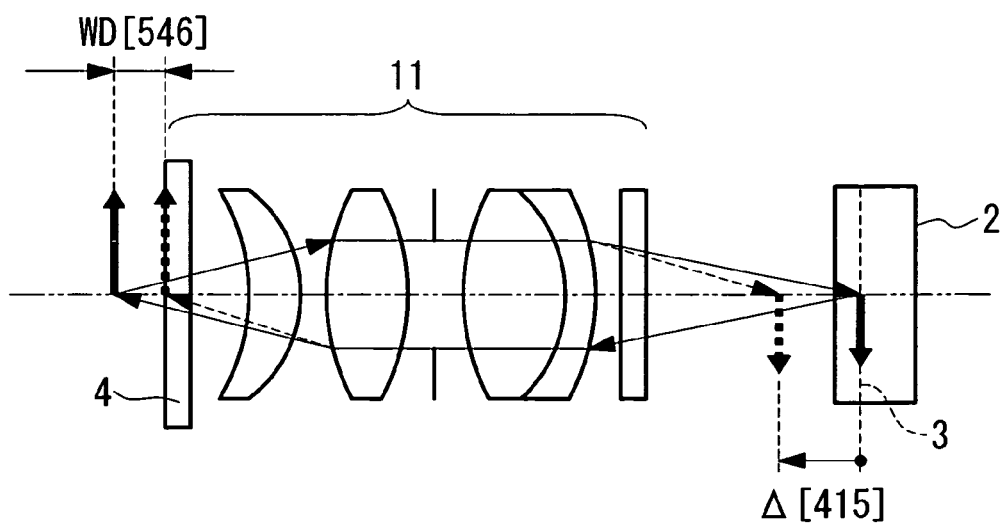
FIG. 7 illustrates the observation optical system according to the second embodiment of the present invention with residual longitudinal chromatic aberration.

FIG. 7 illustrates the observation optical system according to this embodiment, having residual longitudinal chromatic aberration. More specifically, FIG. 7 illustrates a residual state of longitudinal chromatic aberration according to thirteenth to eighteenth examples of the second embodiment, which are particularly suitable for magnified observation.

An objective optical system 11 including a plurality of lenses and an aperture stop, as shown in FIG. 7, is configured to form an image of an object on an image-acquisition device 2. For standard visible-light observation, the focal position is located at an image-acquisition plane 3 of the image-acquisition device 2 for a light having a wavelength of 546 nm (e-line), which is the central wavelength of the visible range. For light having a wavelength of 415 nm, images are formed closer to the object than the image-acquisition plane 3. In other words, similar to the first embodiment, longitudinal chromatic aberration remains due to undercorrection.

In FIG. 7, the arrows shown in heavy solid lines represent the object position and image position for light having a wavelength of 546 nm, and the arrows shown in heavy dotted lines represent the object position and image position for light having a wavelength of 415 nm. In the embodiment shown in FIG. 7, since contact with the mucous membrane of a living organism is assumed, a focal plane (conjugate plane of the image-acquisition plane) of 415 nm light is set to the object-side surface of a cover glass 4.

Therefore, in this embodiment, WD[415] is always zero. Since the longitudinal chromatic aberration remains due to undercorrection, the focal position of light having a wavelength longer than 415 nm moves towards the object. Accordingly, for the focal position of 546 nm light is only WD[546] away from the object-side surface of the cover glass 4.

When the distance between the mucous membrane and the cover glass 4 is maintained by using a tip attachment, WD[415] can be set to a value other than zero.

Numeric data according to the thirteenth to eighteenth examples are shown in Table 3 below.

TABLE 3

| Example | β | f | Δ[415] | Δ[415]/f | WD[415] | WD[436] | WD[486] | WD[546] |
|---|---|---|---|---|---|---|---|---|
| 13 | −0.55 | 2.057 | −0.218 | −0.106 | 0 | 0.152 | 0.441 | 0.688 |
| 14 | −0.75 | 3.874 | −0.223 | −0.058 | 0 | 0.100 | 0.277 | 0.416 |
| 15 | −0.93 | 2.829 | −0.252 | −0.089 | 0 | 0.071 | 0.198 | 0.299 |
| 16 | −1.46 | 3.179 | −0.313 | −0.098 | 0 | 0.038 | 0.104 | 0.157 |
| 17 | −1.99 | 2.920 | −0.384 | −0.131 | 0 | 0.025 | 0.069 | 0.104 |
| 18 | −2.91 | 2.292 | −0.525 | −0.229 | 0 | 0.016 | 0.045 | 0.068 |

β: paraxial lateral magnification for 546 nm light
WD[436]: focused object distance for 436 nm (g-line) light
WD[486]: focused object distance for 486 nm (g-line) light In Table 3, each WD[wavelength] represents a value in air. To convert the value into a value in a living body, the value shown in the table is multiplied by 1.333 (refractive index for water). The thirteenth to eighteenth examples satisfy the condition of Formula (3), 0.05 mm<WD[546]−WD[415]<0.75 mm. As is apparent from Table 3, in the thirteenth to eighteenth examples, the wavelength and the focused object distance have a monotonically increasing relationship, and WD[546]−WD[415] is a parameter representing the identifiable range in the depth direction.

If this condition can be realized in a narrow depth of field observation optical system, by selecting a narrow band as the waveband used for image acquisition, a slice image of a predetermined depth can be obtained. There are various different mucous membranes in a living body. In the case of colon cancer, one approach is to set thresholds of invasion diagnosis at a mucous membrane depth of about 0.2 mm to about 0.3 mm and at near 1 mm. When the thirteenth example is applied to the case of colon cancer, an image of the mucous membrane surface can be obtained by narrow band light of 415 nm, a slice image at a depth of 0.203 mm (0.152 mm×1.333) can be obtained by acquiring an image of narrow band light of 436 nm, and a slice image at a depth of 0.917 mm (0.688 mm×1.333) can be obtained by acquiring an image of narrow band light of 546 nm.

In this case, as shown in FIG. 3B, it is very useful if the central wavelengths of the B2 band, the G2 band, and the R2 band are set at 415 nm, 436 nm, and 546 nm, respectively, and each band image is displayed independently. Furthermore, by combining the illumination system with a spectral apparatus or a narrow band light-emitting element, such as a LED or a laser diode, of different wavelengths, more slice images can be obtained.

A high-magnification setting, such as that used in the eighteenth example, is useful for research purposes because analysis can be carried out with high depth-resolution near the surface layer of the mucous membrane, and in-vivo analysis similar to a pathology test can be carried out.

When WD[546]−WD[415]<0.05 mm, the movement of the focal position for each wavelength is too small for identifying the mucous layer, whereas when WD[546]−WD[415] >0.75 mm, the resolution in the depth direction is too coarse.

Since the orientation required for inserting the endoscope cannot be maintained only by the observation optical system, according to the thirteenth to eighteenth examples, the observation optical system is mounted on the endoscope together with a wide-angle observation optical system. Therefore, it is not necessary to switch to standard visible-light observation.

What is claimed is:

1. An endoscope comprising:
   an observation optical system compatible with both standard visible-light observation and blood-vessel-enhancement observation whose main component of a displayed image is an absorption peak of hemoglobin present in a waveband lower than 480 nm,
   wherein the endoscope observation optical system satisfying Formula (1) below for the focal position during standard visible-light observation:

$$-0.25 < \Delta[415]/f < -0.02 \tag{1}$$

where $\Delta[415]$ represents the longitudinal chromatic aberration of light having a wavelength of 415 nm (when light having a wavelength of 546 nm is used as a reference), and f represents the focal length of the entire observation optical system for light having a wavelength of 546 nm.

2. The endoscope according to claim 1, wherein the observation optical system satisfies Formula (2) below:

$$-0.15 < \Delta[415]/f < -0.05 \tag{2}$$

* * * * *